United States Patent [19]
Rault et al.

[11] Patent Number: 5,659,874
[45] Date of Patent: Aug. 19, 1997

[54] DEVICE FOR CONDUCTING CHEMICAL OPERATIONS

[76] Inventors: Sylvain Jean-Marie Rault, 5 Rue Pierre Cingal, 14370 Moult; Jean-Claude Derobert, 6 Rue Jean Mermoz, 14550 Blain-Sur-Orne, both of France

[21] Appl. No.: 703,936

[22] Filed: Aug. 28, 1996

Related U.S. Application Data

[63] Continuation of Ser. No. 140,409, Oct. 25, 1993, abandoned.

[30] Foreign Application Priority Data

Oct. 30, 1992 [FR] France .................................. 92 13046

[51] Int. Cl.$^6$ ........................................................ B01J 19/12
[52] U.S. Cl. ........................ 422/186; 422/906; 219/679; 219/756; 219/429; 219/438
[58] Field of Search ............................... 422/186, 906; 34/259; 219/678, 679, 756, 429, 438; 204/157.43, 157.63

[56] References Cited

U.S. PATENT DOCUMENTS

| | | | |
|---|---|---|---|
| 3,830,893 | 8/1974 | Steingiser | 264/25 |
| 3,963,420 | 6/1976 | Matsumoto et al. | 23/230 R |
| 4,080,168 | 3/1978 | Abu-Samra et al. | 23/230 R |
| 4,165,773 | 8/1979 | Coombe | 149/109.6 |
| 4,347,216 | 8/1982 | Kawasaki et al. | 422/788 |
| 4,363,639 | 12/1982 | Gladon | 55/95 |
| 4,673,560 | 6/1987 | Masse et al. | 423/532 |
| 5,322,603 | 6/1994 | Kameda et al. | 204/158.2 |
| 5,382,414 | 1/1995 | Lautenschläger | 422/186 |
| 5,387,397 | 2/1995 | Strauss et al. | 422/129 |
| 5,407,641 | 4/1995 | Katschnig et al. | 422/107 |

FOREIGN PATENT DOCUMENTS

| | | |
|---|---|---|
| 0155893 | 9/1985 | European Pat. Off. . |
| 0249500 | 12/1987 | European Pat. Off. . |
| 0387161 | 9/1990 | European Pat. Off. . |

OTHER PUBLICATIONS

Fisher Catalog, 1992, pp. 788–789.

*Primary Examiner*—Charles T. Jordan
*Assistant Examiner*—Daniel Jenkins
*Attorney, Agent, or Firm*—Young & Thompson

[57] ABSTRACT

Device for conducting chemical operations, comprising a working chamber (1) delimited by a top (2), a bottom (3), side walls (4, 5) and a door, a microwave energy generator (6) for the chamber, and a reactor (7) having at least one neck (8) and resting in the chamber on a support (9). The chamber (1) is pierced by at least one passage (12) which permits connecting the neck (8) of the reactor (7) with a connection conduit (13) secured to an external device for conducting a chemical reaction. The chamber is also pierced by two other passages (15 and 16) adapted respectively to permit the connection of two other necks (17 and 18) to the reactor (7).

8 Claims, 2 Drawing Sheets

DEVICE FOR CONDUCTING CHEMICAL OPERATIONS

This application is a continuation of application Ser. No. 08/140,409, filed Oct. 25, 1993, now abandoned.

FIELD OF THE INVENTION

The invention relates to a device for conducting chemical operations comprising a working chamber delimited by a top, a bottom, side walls and a door, a generator of microwave energy for said chamber and a reactor having at least one neck and resting in said chamber on a support.

BACKGROUND OF THE INVENTION

Until now, such a device permitted carrying out only very small volume reactions and without the possibility of continuously conducting said reactions. Thus, such a device permitted only carrying out tests, generally in a hermetically sealed and protected reactor, and to augment the acceleration of chemical syntheses under the effect of microwave heating.

SUMMARY OF THE INVENTION

The present invention has for its object to provide a device which can conduct any current operations in chemistry in a manner analogous to those conducted in a conventional laboratory.

According to the invention, the chamber is pierced with at least one passage which permits interconnecting the neck of the reactor with a connection conduit secured to an external device for conducting a chemical reaction.

Thanks to the invention, there can be conducted from outside the chamber the chemical reaction in the reactor and there can be effected particularly either batch operations in which the external device comprises a vapor condenser and a liquid injector, or operations with distillation in which the external device comprises a distillation column and a liquid injector.

According to a modification, the reactor can be replaced by a coil whose ends are connected respectively to two passageway holes provided in the chamber thus permitting continuous syntheses.

BRIEF DESCRIPTION OF THE DRAWINGS

The characteristics and advantages of the invention will appear more clearly from the description which follows, by way of example, with reference to the accompanying drawings, in which.

DETAILED DESCRIPTION OF THE INVENTION

Figure 1:
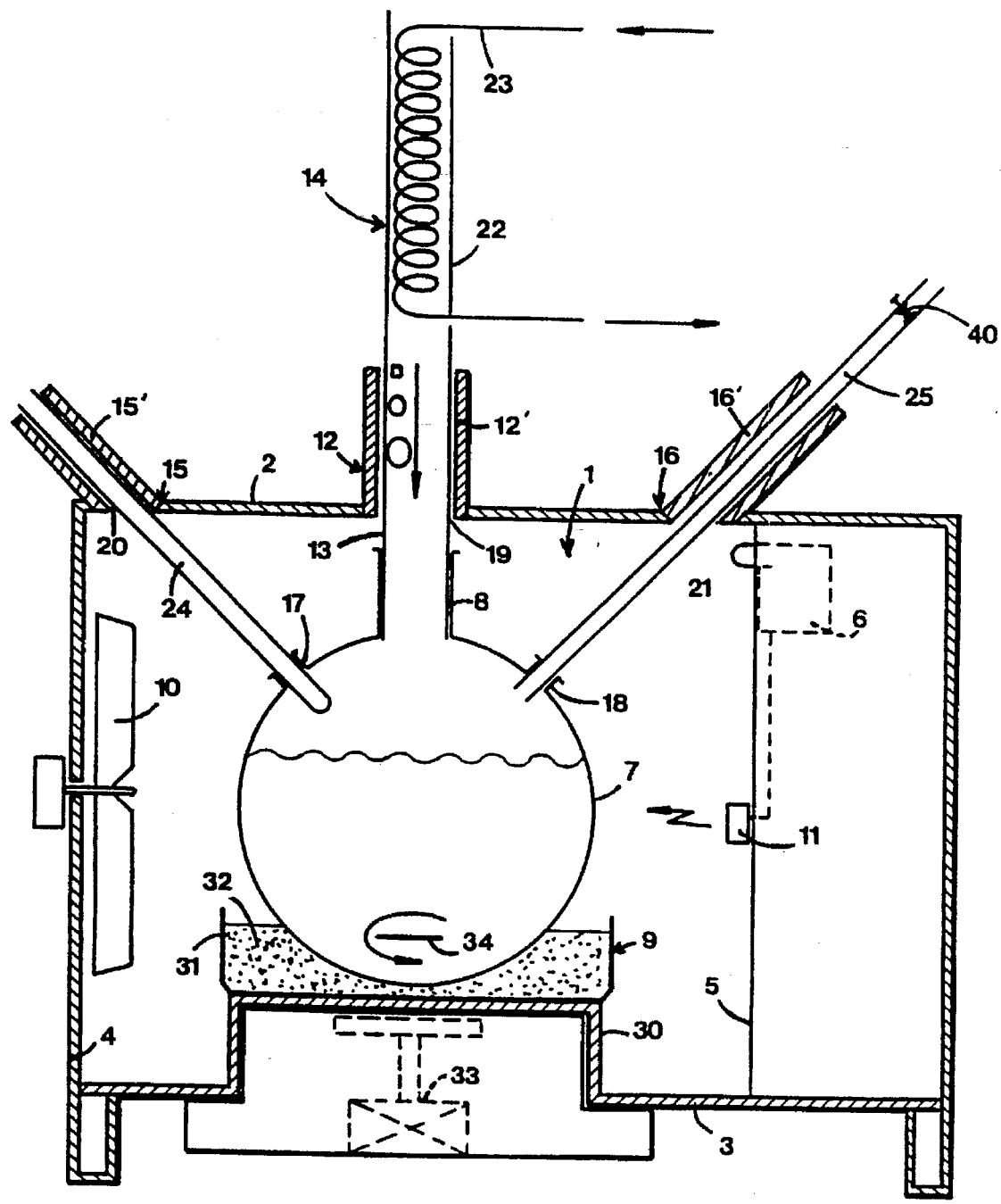
FIG. 1 is a vertical schematic cross sectional view of a device according to the invention used to carry out constant volume reactions.
Figure 2:
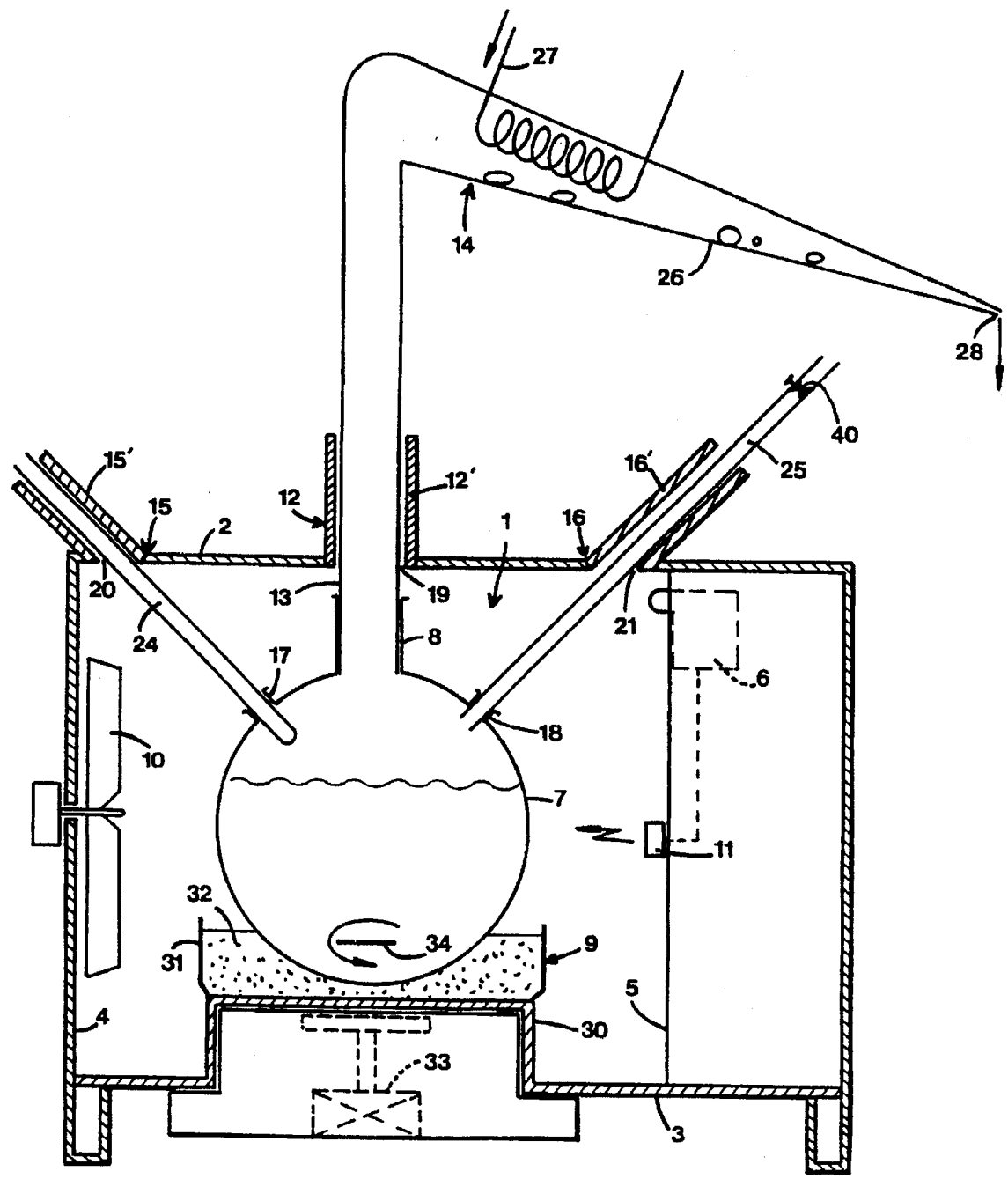
FIG. 2 is a view of a device analogous to that shown in FIG. 1, but used to carry out reactions with distillation.

The device shown in FIGS. 1 and 2 comprises a working chamber 1 delimited by a top 2, a bottom 3, side walls 4, 5 and a door (not shown), a microwave energy generator 6 for said chamber, and a reactor 7 of the open type having at least one neck 8 and resting in said chamber 1 on a support 9. This chamber 1 can be provided in conventional fashion with a rotatable wave stirrer 10, as well as an infrared temperature detector 11 adapted to ensure automatic control of the generator 6. This generator 6 can operate, either with continuous power, or with variable or variable sequential power, as a function of the chemical reactions to be conducted. The reactor can have any shape known per se in the field of chemistry and in particular have a spherical shape as shown.

According to the invention, the chamber 1 is pierced by at least one passage 12 which permits connecting the neck 8 of the reactor with a connection conduit 13 secured to an external device 14 for conducting the chemical reaction.

As will be seen in FIGS. 1 and 2, the top 2 of the chamber 1 is pierced by three passages, the passage 12 extending vertically and two other lateral passages 15 and 16 adapted respectively to permit connections with the necks of a flask of standard type, which is to say the neck 8 directed vertically and the necks 17 and 18 oriented appropriately. These passages 12, 15 and 16 each comprise a device for preventing the escape of microwaves outside the chamber. These passages are comprised by tubes 12', 15', 16' which open into openings 19, 20, 21 provided for example in the top 2 of the chamber.

According to a modified embodiment (not shown), each tube 12', 15', 16' is mounted swingably for example by means of a universal connection, on the chamber so as to permit an articulation with necks of different types of flasks. These tubes therefore constitute wave guides with cutoffs and permit attenuating the electromagnetic waves to render these outlets compatible with safety standards in force. This attenuation of the waves in the cylindrical tube is known per se and depends on two factors $a/\lambda o$ and $z/o$ in which a is the radius of the tube, z is the axial length, and $\lambda o$ represents the wavelengths to be attenuated. The choice of radius of the guide is such that the wavelength to be attenuated $\lambda o$ will be greater than the wavelength with cutoff of the TEM mode. For example for a wavelength $\lambda o=12.2$ cm, there will be chosen $a=2$ cm and $z=20$ cm. The mode of computation has for example been described in the book entitled "Microwave Measurements" by E. L. Ginzton, McGraw-Hill Book Company, 1957.

Thanks to these tuned tubes, it will be understood that the use of open reactors poses no problem for the user and therefore permits conducting all the known chemical operations and more particularly those of organic synthesis.

According to a first embodiment shown in FIG. 1, the device is used to carry out constant volume reactions. The external device 14 comprises for this purpose a vapor condenser 22 whose conduit 13 passes through the tube 12' and enters in a substantially sealed manner into the neck 8 of the reactor 7, and which is cooled by a circulation of water 23 condensing the solvent vapors. The liquid thus formed returns to the reactor 7 which thus retains a practically constant volume of liquid. The tubes 15' and 16' permit respectively the passage of a thermometer or a probe 24 to penetrate in a sealed manner into the neck 17, and the passage of a conduit 25 into the neck 18 to introduce solids, gases or liquids during the reaction, said conduit 25 being provided with an opening-closing valve 40.

According to a second embodiment shown in FIG. 2, the device is used to carry out reactions with distillation and comprises for this purpose a distillation column 26 whose conduit 13 passes through the tube 12' and enters in sealed manner into the neck 8 of the reactor 7, and which is cooled by a water circulation 27, the distilled liquid flowing through the opening 28. The tubes 15' and 16' permit respectively the passage through the neck 17 of the thermometer or of the probe 24, and the passage of a conduit 25 for the introduction of liquid.

Thanks to this embodiment there can also be envisioned the continuous treatment of a large quantity of liquid comprising, for example, a solvent and reagents, the distillation permitting recovering the solvent while the accompanying products accumulate in the base of the reactor. This embodiment permits rectification and recovery of the solvents.

So as to improve the reactions in the reactor 7, the invention provides that the wall of bottom 3 has a suitable raised elevation 30 adapted to place the reactor in working position in the central region of the chamber 1. Thanks to this elevation, there can be used reactors of the open type and of somewhat different volume, while keeping a support of the defined type; this is to say a support having properties relative to microwaves such as: light load, permeability, stability, dielectric material ... Such a support 9 comprises a pan 31 preferably of glass transparent to microwaves containing a pulverulent material 32 such as for example "Fontainebleau" sand.

In another embodiment (not shown), said support 9 can have a certain load so as to be able to treat small volumes.

In a preferred embodiment and so as to obtain good homogenization of the contents of the reactor 7, the invention provides the chamber 1 with a magnetic agitator comprising a rotatable motor means 33 arranged in the raised elevation 30 and a magnet 34 provided in the reactor 7. To this end, the wall of bottom 3 is formed preferably of a non-magnetic material. Preferably for reasons of temperature resistance, rigidity and cleanliness, the bottom is of stainless steel.

Thus the device according to the invention permits using open reactors of large volume to carry out synthetic organic reactions which, under normal laboratory conditions, could not be obtained or would be obtained with very low yield, less than 5%. For example, there can be carried out a reaction of the type:

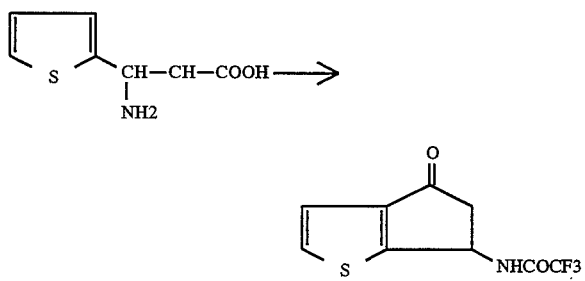

Such a device because of its possibility of conducting the reaction through the passages of the chamber also permits the preparation of new compounds principally of heterocyclic nature.

Moreover, reactions of the type:

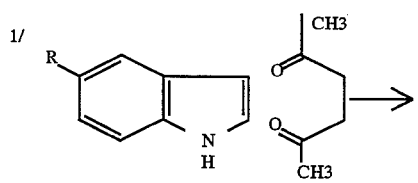

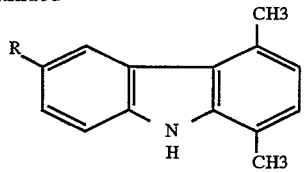

or of the type

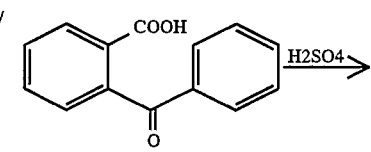

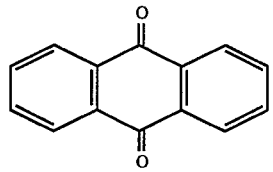

can be carried out with substantially quantitative yields [ρ=50 to 85% for quantities of the order of 100 grams] with application of microwaves for 5 minutes.

Thanks to the device according to the invention, it will be understood that industrial applications can be envisaged.

What is claimed is:

1. Apparatus for conducting chemical operations at atmospheric pressure including synthetic organic reactions, comprising a working chamber delimited by a top, a bottom, side walls and a door, a microwave energy generator for said chamber, and a reactor having at least one neck and resting in said chamber on a support, said chamber being pierced by a first passage which permits connecting the neck of the reactor with a connection conduit secured to an external device for conducting a substantially constant volume chemical reaction, and pierced by a second and third passage adapted respectively to permit the connection of two other necks to the reactor, said second passage constructed and arranged for allowing passage of a thermometer or probe into said reactor, and wherein each of said passages comprises a device for preventing escape of microwaves outside the chamber.

2. Apparatus according to claim 1, wherein each of said passages comprises a tube of a dimension suitable to serve both as a connection guide and as the device for preventing escape of microwaves.

3. Apparatus according to claim 2, wherein each tube is mounted articulatedly on the chamber so as to permit the connection with different necks of flasks.

4. Apparatus according to claim 1, wherein the support comprises a dish transparent to microwaves and containing a pulverulent material.

5. Apparatus according to claim 4, wherein the pulverulent material is sand.

6. Apparatus according to claim 1, wherein the bottom of the chamber has a raised portion of a height such that the reactor resting on said support is disposed in a central portion of said chamber.

7. Apparatus according to claim 6, wherein the chamber has a magnetic agitator for the reactor and the bottom is constituted by a non-magnetic material.

8. Apparatus according to claim 7, wherein the magnetic agitator comprises a motor arranged in the raised portion.

* * * * *